United States Patent [19]
Garcia

[11] 4,436,512
[45] Mar. 13, 1984

[54] DEVICE FOR FIXING DRILL BITS INTO THE HEAD OF AIR MOTORS FOR HAND-HELD DENTISTS' TOOLS

[75] Inventor: Philippe Garcia, Besancon, France

[73] Assignee: Micro-Mega S. A., Besancon, France

[21] Appl. No.: 322,411

[22] Filed: Nov. 18, 1981

[30] Foreign Application Priority Data

Dec. 22, 1980 [FR] France ............................ 80 27642
Feb. 10, 1981 [FR] France ............................ 81 02734
Feb. 10, 1981 [FR] France ............................ 81 02735

[51] Int. Cl.³ .................................................. A61C 1/14
[52] U.S. Cl. ............................................................ 433/129
[58] Field of Search .................. 433/127, 129; 279/102, 279/9, 95, 96, 46, 1 SG

[56] References Cited

U.S. PATENT DOCUMENTS

3,074,167 1/1963 Turchi et al. .................... 433/129
3,314,153 4/1967 Maurer .............................. 433/129

*Primary Examiner*—Robert Peshock
*Attorney, Agent, or Firm*—Robert E. Burns; Emmanuel J. Lobato; Bruce L. Adams

[57] ABSTRACT

Device for fixing drill bits into the head of air motors for hand-held dentists' tools, of the type incorporating a clip in the rotor inside which the shank of the drill bit is inserted. The fixing clip (6) includes longitudinal slits (7) and is acted on at one of its ends by an elastic means which tends to close the head (10) of the clip (6) on to the drill shank by the cooperation of an inclined surface (11) formed on the head of the clip with a matching inclined surface (12) formed on the inside face of the rotor (2), the head of the air motor being further provided with means which allow the shank of the drill to be released, by compressing said elastic means.

12 Claims, 6 Drawing Figures

DEVICE FOR FIXING DRILL BITS INTO THE HEAD OF AIR MOTORS FOR HAND-HELD DENTISTS' TOOLS

The present invention relates to a device for fixing drill bits into the head of air motors for hand-held dentists' tools, of the type including a clip in the rotor inside which the shank of the bur or drill bit is inserted.

One of the problems involved in a hand-held piece of dental equipment is that of driving a tool (drill) which is held by adequate means in the head of the hand tool using a motor.

The drill bit must however be fixed in a releasable manner so that it can easily be changed as desired, without the need for an excessive number of operations, in order to replace it by another tool needed for the actual dental operation which is being carried out, or simply for allowing the hand tool to be cleaned.

The first air motor heads which were put forward included, at the centre of the rotor, a threaded tube in plastics material. The central inner hole of this tube had a diameter which was slightly smaller than that of the shank of the drill so that the latter could be forced in by taking advantage of the elasticity of the plastics material constituting the tube. This friction was used to drive the drill bit in rotation by the tube which was rigidly fixed to the air motor.

This system did suffer from certain disadvantages, and particularly suffered from rapid and excessive wear.

More recently multiple systems using metal clips have been proposed. The disadvantage of all such proposed devices resides in the fact that, in order to provide for clamping of the metal jaw on to the shank of the drill bits and other apparatuses, keys or other components were necessary, the use of which was particularly inconvenient, particularly for the dental practitioner.

Such devices using a metal clip and their associated components of this type are for example, described in West German unexamined Patent Application Nos. 2,555,617 and 2,832,157.

The present invention has the aim of overcoming these various disadvantages and provides an effective system for fixing dental drill bits in place, which can be released in a simple manner without the use of a specific accessory component.

In accordance with the invention, this result is obtained with a device for fixing drill bits into the heads of air motors for dentists hand tools, of the type which include a clip in the rotor inside of which the shank of the drill is inserted, characterized in that the fixing clip includes longitudinal slits and is acted upon at one of its ends by an elastic means which tends to close the head of the clip on to the shank of the drill using cooperation of an inclined surface on the head of the clip with a corresponding inclined surface on the inside face of the rotor, the head of the hand tool being further provided with means which allow the shank of the drill to be released by compressing said elastic means.

The insertion of a drill bit is consequently extremely simple. By compressing the elastic means, the insertion of the shank of the drill bit is possible. As soon as the pressure on the elastic means is released, these compress the head of the clip and, by using the system of corresponding inclined surfaces, this pressure locks the shank of the drill bit in position.

The elastic means can be of any desired type, for example a simple coil spring, which, at one end, acts on a ring which is screwed or force-fitted on to the head of the hand tool, and at the other end on the head of the clip.

Advantageously and according to a further characteristic of the invention, the elastic means employ a specially designed structure in the form of a cylinder which acts exactly like a coil spring, the cylinder being provided with cut-out portions at alternate sectors arranged at 90° with respect to each other.

Release of the drill shank, according to a further advantageous characteristic of the invention is achieved by rotating a button which is fitted over the upper end of the head of the air motor. Obviously, when in such position that the shank of the drill bit is locked in place, during use, this button is not in engagement with the actual rotor and is not driven in rotation together with the latter.

According to one variation in the manner of carrying out the invention, the means for releasing the shank of the drill essentially consists of a button fitting over the head of the air motor, said button being screwed on to the end portion of the end bearing plate which holds the air motor, and includes two pins on its inner face which are arranged radially and symmetrically with respect to the centre of the button.

These pins thus become displaced when the button is rotated, in annular windows in the end bearing plate which carries the air motor and which is screwed on to the body of the air drill head.

A sping device is used to prevent any rotation which could be brought about as the result of vibration occurring during operation of the air motor.

According to a further embodiment of the invention, one could also provide a fixing clip which has a quite specific structure and includes longitudinal slits.

In this embodiment, the clip is made up by a plurality of longitudinal segments which are independent of each other at the upper end of the clip and separated from each other at their base by intermediate lugs.

The invention will be more readily understood when reference is made to the description which follows in conjunction with the attached drawings in which.

Figure 1:
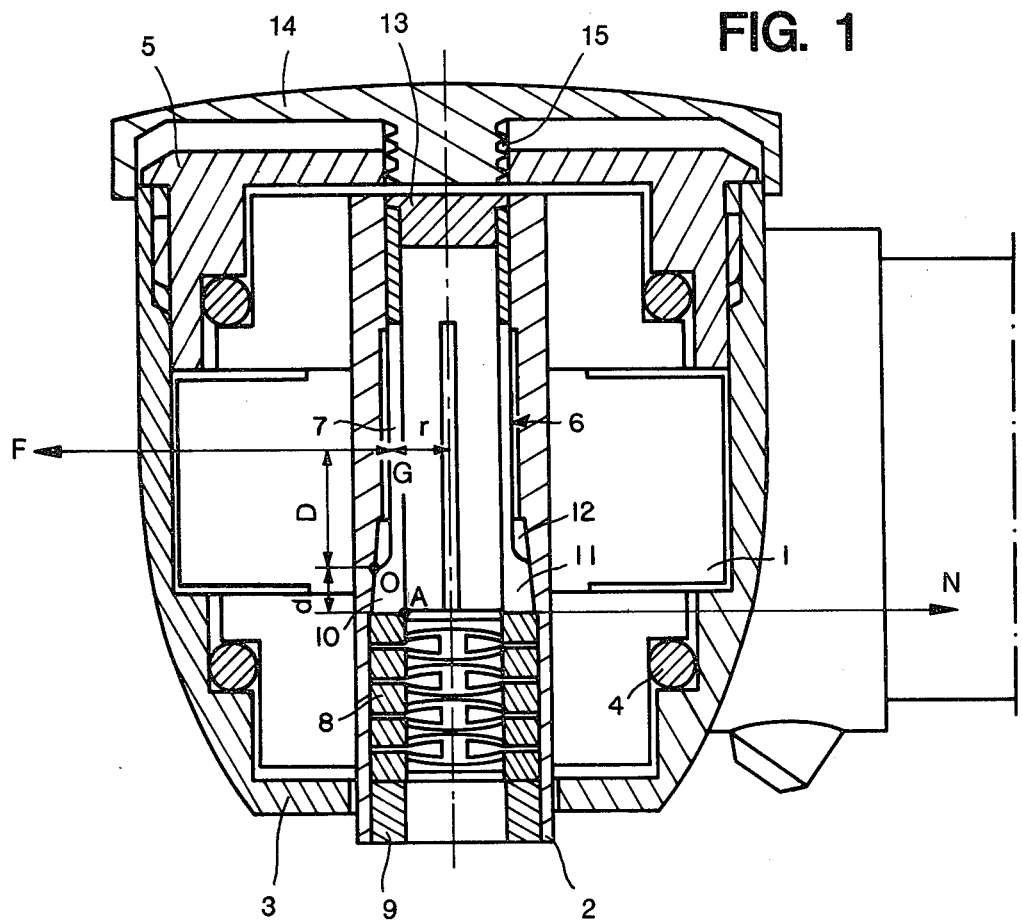
FIG. 1 is a longitudinal sectional view of the air motor head of a hand tool equipped with a device according to the invention.

FIG. 1 shows the head of an air motor for a hand tool of conventional construction which is known per se. The inlet for the compressed air has not been shown. The jet of compressed air strikes the vanes (1) of the rotor which are cut according to the desired configuration in a crown which is force fitted on to a tube (2) which constitutes the actual body of the rotor. This rotor, in a completely conventional manner, rotates inside the body of the air motor (3) on bearings (4)

which may either consist of ball bearing races or of fluid bearings. This whole assembly is held in the air motor, using, for example, an end bearing plate (5) which is screwed into the body of the air motor head (3).

All that has been described above is completely conventional and should not be considered as being limiting.

Figure 2:
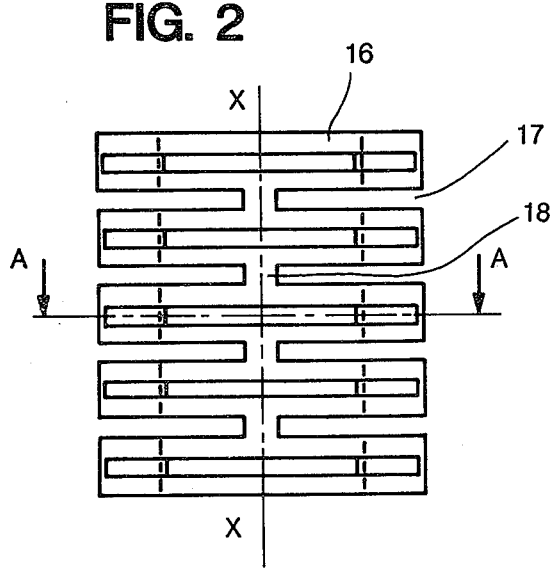
FIG. 2 is an enlarged view of a special spring which is used in the attaching system according to the invention.
Figure 3:
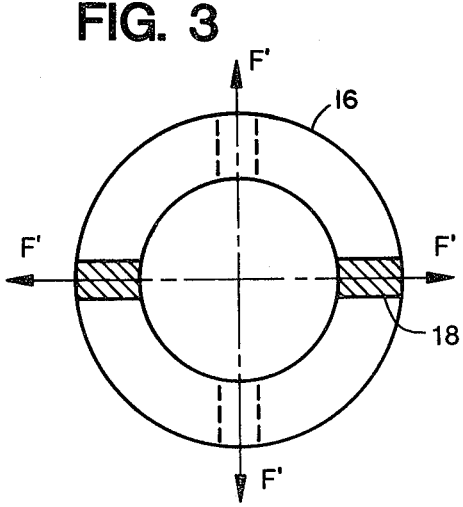
FIG. 3 is a sectional view according to A—A in FIG. 2.

As has been indicated above, the body of the rotor is made up by a tube (2). A clip (6) is provided inside this tube, and the clip includes longitudinal slits (7) and a spring (8). This spring can, for example, be made up by a coil spring or even by a tube in plastics material, or finally it may be a spring having a specific shape which is shown in FIGS. 2 and 3 in greater detail; this will be described below. The latter will nevertheless essentially act as a coil spring. As a result of its particular structure it will however also be involved in keeping the shank of the drill bit in place.

The spring (8) abuts at one end on a closure member (9) which is screwed or force-fitted onto the tube (2) of the rotor, and at the other end, against the forward end (10) of the clip (6). The forward end (10) of the clip (6) has an exterior shaping in the form of an inclined surface (11) and this cooperates with a corresponding inclined surface (12) formed on the inside face of the rotor body (2).

At the other end of the clip (6) a closure member (13) is fitted in place. The back end of the air motor head has a button (14) fitted around it which is screwed at (15) into the end bearing plates (5) so that it is consequently able to push against the closure member (13) of the clip (6). When this is done, the spring (8) becomes compressed thus releasing the inclined surface (11) at the forward end of the clip from the corresponding inclined surface (12) which has the effect of opening the clip and thus releasing the shank of the drill bit.

When the drill is operating, the button 14 must obviously not be in contact with the rotor. It is moved away from the latter by any known drive release member which is known per se, for example a sprung lug.

The shank of the drill bits is consequently clamped in the clip (6) through the action of spring (8) alone. This constitutes the main original feature of the invention.

Reference will now be made in particular to FIGS. 2 and 3. The spring which is shown there is made up by a tube of metal (16) in which hollow portions (17) have been cut out and these alternate at 90° to each other.

This highly specific and original structure finally provides a cylinder which is pierced in such a way that the series of small discs which are connected pairwise by bridges of solid material (18) become flexed when it is subject to compression, which gives it the form which has been shown in FIG. 1.

The essential advantage of such spring consists in the fact, that by virtue of the perfect symmetry of its structure, perfect balance is achieved, this being absolutely essential at speeds of rotation which may reach 200,000 revolutions per minute when actually working and even 400,000 r.p.m. when running in the unloaded state.

Additionally, this structure also provides an additional complementary frictional force on the shank of the drill bit.

In fact, resulting from the centrifugal forces operating, the masses M of the bridges of solid material (18) which connect the small flexible washers together tend to become displaced from the axis of the tube, which tend to cause deformation of each small washer, as a result of which there is an increase of friction on the shank of the drill bit. This is shown diagramatically in FIG. 3 where the arrows F' represent the centrifugal force acting on each solid material bridge (18). In actual fact, the central passage tends to approach a section which is square in shape, which will be readily understood.

Concerning the symmetry of the spring in FIG. 2, it will be noted that the centre of gravity of the spring is located on the axis x—x, which allow the possibility of rotation about this axis without running out-of-true occuring, in other words without lack of balance.

The special structure of the actual clip provides a further additional frictional force on the shank of the drill bit, as it becomes deformed under the effects of centrifugal force. This constitutes an essential characteristic of the invention.

The results obtained are remarkable, and by way of illustration, an example is given below of the evaluation of the force necessary to extract the drill bit from the clip during rotation, for a force of extraction under non-running conditions which can be set to a desired value, as a function of the choice of spring, which for example can be 2 kg.

If the following meanings are attributed to the symbols below:

G: centre of gravity of an arm of the clip.
O: point of pivoting or point of abutment of the lever.
A: point of application of the radial force N defined below.
m: mass of an arm of the clip.
$\omega$: velocity of rotation.
F: centrifugal force.
N: supplementary radial force due to the centrifugal force.

then the following relationship substantially holds:
D=GO
d=OA

D and d being shown in FIG. 1 as respectively, the distances between, firstly, the transverse plane of the point G, that of the point O and, secondly, the transverse plane of point O and that of point A.

The force F applied at G has a value of:
$F = m\omega^2 r$, r being the distance of G from the axis.

Now the arm comes to rest, under the action of force F, at O which displaces the point A towards the axis of the rotor. The pressure force N thus produced is inversely proportional to the distances OA and OG, which in other words ae connected by the relationship:

$$N = OG/OA \; F = D/dF$$

Consequently the value of N is:

$$N = D/d \; m\omega^2 r$$

For:
m=6 mg
D/d=5
and
a speed of rotation of 200,000 revolutions per minute, a value of N is attained which is closed to 3 kg. At 400,000 revolutions per minute, this value will approach 6 kg.

Figure 4:
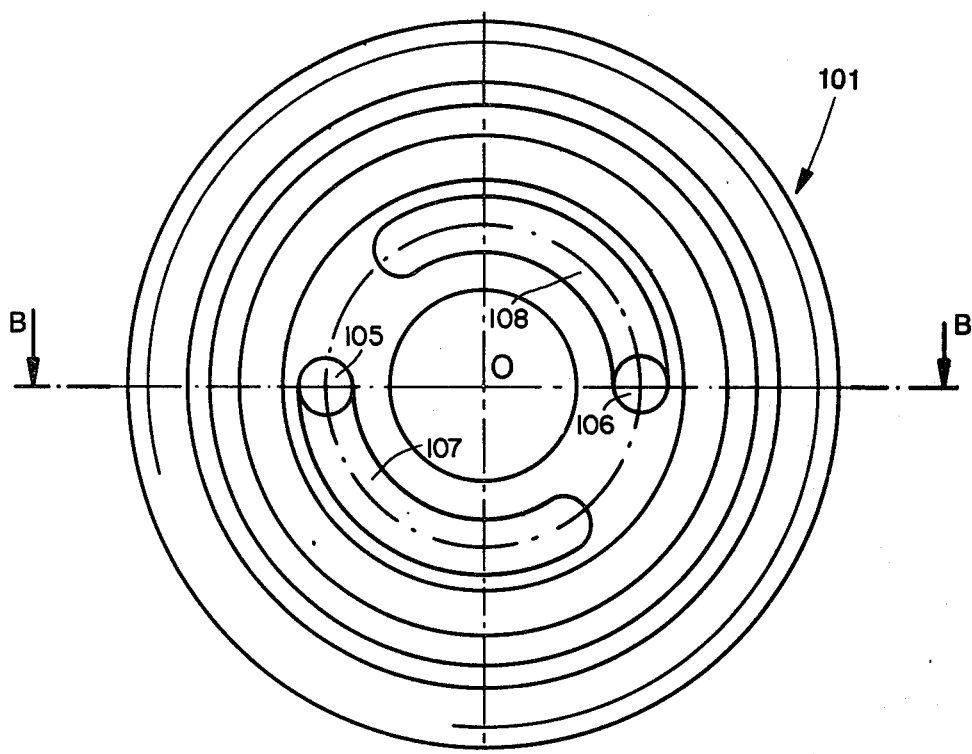
FIG. 4 is a view fron below of a button according to one alternative embodiment of the invention, with the end bearing plate which supports the air motor.
Figure 5:
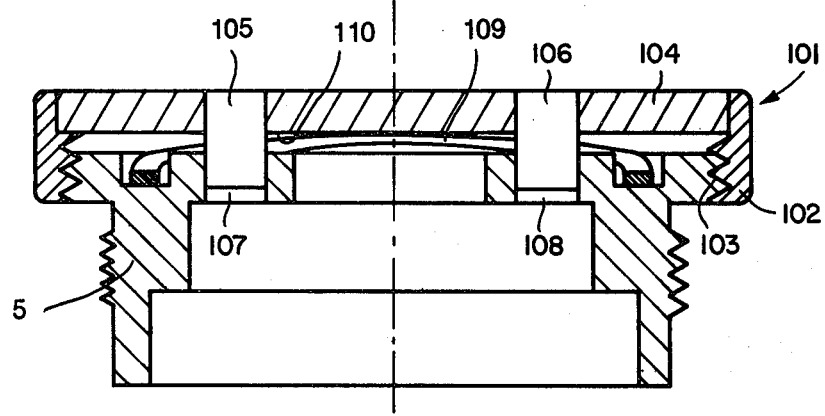
FIG. 5 is a sectional view according to B—B in FIG. 4.

In the alternative embodiment shown in FIGS. 4 and 5, the button (101) essentially includes an outer crown (102), which is provided with an inner thread (103), and a plate (104) which is force-fitted on to said crown.

Two cylindrical pins, (105, 106) are fixed on to the inside face of the plate (104) in a rigid manner and these are arranged radially and symmetrically with respect to the centre O of the plate (104).

The button (101) is screwed using its thread (103) on to the end bearing plate (5) which itself is screwed into the body of the air motor. The pins (105, 106) are adapted to become displaced under rotation when the button is being screwed up or unscrewed, in symmetrical annular slots (107, 108) formed at the upper face of the end bearing plate (5).

Finally, an annular leaf spring (109) bears against the upper portion of the end bearing plate (5) and urges the button (101) in the upwards direction to prevent any rotation which might for example be caused by vibration.

Displacement of the clip is obtained by displacing the base (110) of the closure member which may be for example include a central stud which bears against the end of the clip, or which comes into contact with a clip whose end projects with respect to the end bearing plate (5).

Figure 6:
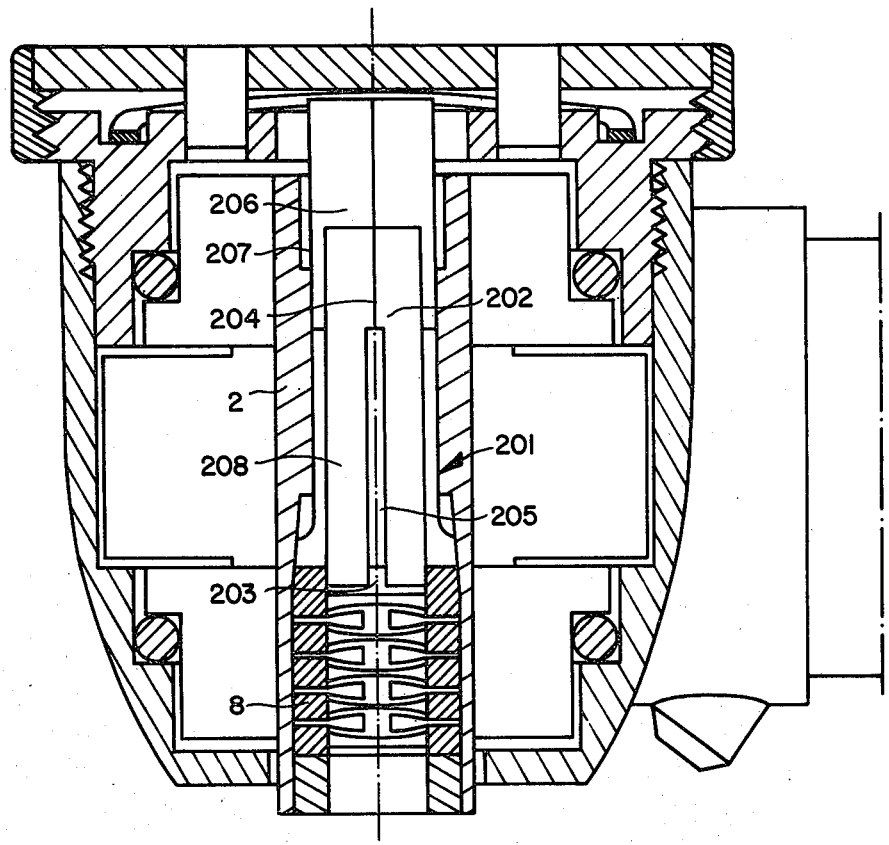
FIG. 6 is a longitudinal sectional view of a further embodiment which employs a different clip.

In the alternative embodiment shown in FIG. 6, a clip having a different structure has been shown. The clip (201) includes a plurality, for example three or four, segments (202) which are similar to segments of a conventional clip but are independent at their upper end.

At their lower end, the segments are separated from each other by intermediate lugs (203) formed on the end of the spring (8). They may bear against each other at the upper end (204), but they may also become spaced from each other at this level and, obviously, throughout the whole of their length by virtue of the grooves (205).

These segments are provided at their upper end with a region (206) which is thicker than the remainder of their body.

This region limits the amount by which the shank of the drill bit is able to penetrate into the clip.

This reinforced region which is consequently heavier further constitutes a mass, the centre of gravity of which is at a point G1 which tends to become displaced away from the central axis when the air motor is rotating.

At this moment, the end region of the segment tends to become bent outwardly and, by pivoting at a point of abutment P made up by an inner widening (207) of the tube (2) of the rotor, causes the lower portion (208) of the clip to bear against the shank of the drill bit. The force which this portion of each segment applies to the shank depends on the mass of the upper portion and on the length of the lever arm.

In FIG. 6, the air motor head has been shown provided with a release button which is similar to that shown in FIGS. 4 and 5. The structure of the button is not important in this discussion, and any other structure can be employed without this leading to departure from the scope of the invention.

I claim:

1. Device for securing a drill bit into the head of an air motor driven dental drill of the type including a housing mounting a rotor having a collet means for receiving the shank of the drill bit and a bit retention means to secure the bit in the collet means, the improvement wherein the retention means (6) includes longitudinal slits (7) and a head portion (10) having an inclined surface (11), the collet means of the rotor (2) having an inclined surface (12) corresponding to said inclined surface (11), a biasing means acting at one end of the retention means (6) to close the head portion (10) of the retention means onto the shank of the drill bit using the cooperation of inclined surface (11) and corresponding inclined surface (12), and a release means to release the shank of the drill bit by compressing the biasing means, said release means comprising a button (14) fitted over the housing and a closure member (13) rigidly fixed at one end of the retention means (6), wherein a turning of said button (14) causes displacement of said closure member (13).

2. Device according to claim 1, wherein during rotation of the drill the button (14) is prevented from rotating by a spring member.

3. Device according to claim 1, wherein the release means comprises a button (101), said button being screwed into the outer portion of an end bearing plate (5) which holds the air motor in the housing, and includes two pins (105, 106) on its inner face which are arranged radially and symmetrically with respect to the center, O, of the button (101).

4. Device according to claim 3 wherein the pins (105, 106) become displaced in annular slots (107, 108) in the end bearing plate (5) when the button (101) is rotated.

5. Device according to claims 3 or 4 wherein the button is retained at an upper position by an annular leaf spring (109) which bears on an upper portion of the end bearing plate (5).

6. Device according to any one of claims 1–5 wherein the biasing means comprises a spring which bears at one end on a closure member fitted onto the rotor (2) and at the other end on the head (10) of the retention means.

7. Device according to any one of claims 1–5 wherein the biasing means comprises a coil spring.

8. Device according to any one of claims 1–5 wherein the biasing means comprises a spring composed of a metal cylinder (16) in which cut-out portions (17) are formed which alternate at 90 degrees forming a series of small plates connected together by bridges of solid material (18).

9. Device according to any one of claims 1–5 wherein the retention means becomes deformed under the effects of centrifugal force to apply an additional force onto the shank of the drill bit.

10. Device according to any one of claims 1–5 wherein the retention means includes a plurality of longitudinal segments (202) which are independent of each other at an upper end of the retention means and separated at a base region by intermediate lugs (203).

11. Device according to any one of claims 1–5 wherein the retention means includes a plurality of longitudinal segments (202) having at an upper end a region (206) which is thicker than the body of said segments.

12. Device according to any one of claims 1–5 wherein the retention means includes a plurality of longitudinal segments (202) which bear against an inner enlarged portion (207) of the tube of the rotor (2).

* * * * *